(12) United States Patent
Mao et al.

(10) Patent No.: US 12,203,088 B2
(45) Date of Patent: Jan. 21, 2025

(54) ROOT-SECRETED PEPTIDE PEP1 IN RICE AND GENE ENCODING THE SAME AND USE THEREOF

(71) Applicant: ZHEJIANG UNIVERSITY, Zhejiang (CN)

(72) Inventors: Chuanzao Mao, Zhejiang (CN); Funing Meng, Zhejiang (CN); Dan Xiang, Zhejiang (CN); Aodi Wang, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 162 days.

(21) Appl. No.: 17/780,930

(22) PCT Filed: Aug. 12, 2021

(86) PCT No.: PCT/CN2021/112192
§ 371 (c)(1),
(2) Date: May 27, 2022

(87) PCT Pub. No.: WO2022/174563
PCT Pub. Date: Aug. 25, 2022

(65) Prior Publication Data
US 2023/0279417 A1    Sep. 7, 2023

(30) Foreign Application Priority Data

Feb. 20, 2021   (CN) .......................... 202110194477.8

(51) Int. Cl.
*A01P 21/00* (2006.01)
*A01H 6/46* (2018.01)
*C07K 14/415* (2006.01)
*C12N 15/82* (2006.01)

(52) U.S. Cl.
CPC ....... *C12N 15/8262* (2013.01); *A01H 6/4636* (2018.05); *A01P 21/00* (2021.08); *C07K 14/415* (2013.01); *Y02A 40/146* (2018.01)

(58) Field of Classification Search
None
See application file for complete search history.

(56) References Cited

FOREIGN PATENT DOCUMENTS

CN        112899300 A    6/2021

OTHER PUBLICATIONS

Huffaker et al. Proceedings of the National Academy of Sciences 103.26 (2006): 10098-10103 (Year: 2006).*
Krol et al. Journal of Biological Chemistry 285.18 (2010): 13471-13479 (Year: 2010).*
Xiang et al. The Plant Journal 107.2 (2021): 480-492 (Year: 2021).*
LOC_Os11g09560; Rice Genome Annotation Project (Year: 2013) http://rice.uga.edu/cgi-bin/gbrowse/rice/?name=LOC_Os11g09560; Available Feb. 6, 2013.*
Matsubayashi et al. Annu. Rev. Plant Biol. 57 (2006): 649-674 (Year: 2006).*
Bartels et al. Journal of experimental botany 66.17 (2015): 5183-5193 (Year: 2015).*
Hander et al. Science 363.6433 (2019): eaar7486 (Year: 2019).*
Jing et al. The Plant Cell 31.8 (2019): 1767-1787 (Year: 2019).*
Shinya, Tomonori, et al. The Plant Journal 94.4 (2018): 626-637. (Year: 2018).*
Guo et al, 2004, Proc. Natl. Acad. Sci. USA 101: 9205-9210 (Year: 2004).*
PCambia1300 Plant Expression Vector. abcam (Year: 2024) https://www.abcam.com/products/vectors/pcambia1300-plant-expression-vector-ab275754.html; accessed Jan. 4, 2024.*
TAIR: AT5G64900 (PROPEP1) (Year: 2002) https://www.arabidopsis.org/servlets/TairObject?id=135136&type=locus.*
Heuermann et al. Frontiers in Plant Science 14 (2023): 1122285 (Year: 2023).*
Lu et al Plant biotechnology journal 15.11 (2017): 1371 (Year: 2017).*
Waterhouse et al; Proceedings of the National Academy of Sciences 95.23 (1998): 13959-13964 (Year: 1998).*
GenBank Accession DQ341412.1 Available Aug. 24, 2006 https://www.ncbi.nlm.nih.gov/nuccore/DQ341412.1 (Year: 2006).*
The State Intellectual Property Office of People's Republic of China, First Office Action, Application No. 202110194477.8, dated Jan. 5, 2022, in 12 pages.
PNAS, Tyrosine-sulfated glycopeptide involved in cellular proliferation and expansion in *Arabidopsis*, Amano, et al., dated Nov. 13, 2007, in 6 pages.
Cold Spring Harbor Symposia on Quantitative Biology, Toward a Systems Analysis of the Root, Benfey, dated 2012, in 6 pages.
Plant Physiology, A Large Family of Genes That Share Homology with CLAVATA3, Cock, et al. dated Jul. 2001, in 4 pages.
Trends in Plant Science, Genetic control of root development in rice, the model cereal, Coudert et al., dated Feb. 12, 2010, in 8 pages.
BMC Genomics, Transcript profiling of crown rootless1 mutant stem base reveals new elements associated with crown root development in rice, Coudert et al., dated 2011, in 12 pages.
PNAS, Suppression of *Arabidopsis* protophloem differentiation and root meristem growth by CLE45 requires the receptor-like kinase BAM3, Depuydt et al., dated Apr. 23, 2013, in 6 pages.

(Continued)

*Primary Examiner* — Bratislav Stankovic
(74) *Attorney, Agent, or Firm* — Procopio, Cory, Hargreaves & Savitch LLP

(57) ABSTRACT

The disclosure isolates and identifies a peptide PEP1 that regulates plant root development and a gene OsPEP1 encoding the same. Exogenous application of PEP1 could inhibit the plant root development. A recombinant expression vector containing the gene or part of the DNA of the gene is obtained, and a transgenic plant with altered root growth and development is obtained by transforming with the recombinant expression vector. Therefore, the peptide can be used as a plant growth regulator, and the gene encoding the same and precursor protein thereof can be used as a potential molecular breeding target for crop improvement, for example, improving crop yield by regulating the growth and development of crop roots.

1 Claim, 5 Drawing Sheets

Specification includes a Sequence Listing.

(56) References Cited

OTHER PUBLICATIONS

Field Crops Research, Development of drought-resistant cultivars using physiomorphological traits in rice, Fukai et al., dated 1995, in 20 pages.
Field Crops Research, Root biology and genetic improvement for drought avoidance in rice, Gowda et al., dated 2011, in 13 pages.
The plant journal, Kinase activity and calmodulin binding are essential for growth signaling by the phytosulfokine receptor PSKR1, Harmann et al., dated Dec. 2, 2013, in 11 pages.
EMBO reports, Perception of root-active CLE peptides requires CORYNE function in the phloem vasculature, Hazak et al., Oct. 19, 2016, in 15 pages.
PCT/ISA/2010, Application No. PCT/CN2021/112192, dated Aug. 12, 2021, in 6 pages.
Journal of Biological Chemistry, The Phytosulfokine (PSK) Receptor is Capable of Guanylate Cyclase Activity and Enabling Cyclic GMP-dependent Signaling in Plants, Kwezi et al., dated Jun. 24, 2011, in 9 pages.
The Plant Cell, Phytosulfokine Regulates Growth in *Arabidopsis* through a Response Module at the Plasma Membrane That Includes Cyclic Nucleotide-Gated Channel 17, H+-ATPase, and BAK1, Ladwig et al., dated Jun. 2015, in 12 pages.
The Plant Cell, SPX4 Negatively Regulates Phosphate Signaling and Homeostasis through Its Interaction with PHR2 in Rice, Lv et al., dated Apr. 2014, in 12 pages.
Www.sciencemag.org, Secreted Peptide Signals Required for Maintenance of Root Stem Cell Niche in *Arabidopsis*, Matsuzaki et al., dated Aug. 27, 2010, in 4 pages.
Springer Open, Molecular Mechanisms of Root Development in Rice, Meng et al., dated 2019, in 10 pages.
Research, A peptide hormone required for Casparian strip diffusion barrier formation in *Arabidopsis* roots, Nakayama et al., dated Jan. 20, 2017, in 4 pages.
Trends in Plant Science, Signaling Peptides and Receptors Coordinating Plant Root Development, Oh et al., dated Apr. 2018, in 15 pages.
Cell Press, Post-embryonic root organogenesis in cereals: branching out from model plants, Orman-Ligeza et al., dated Aug. 2013, in 9 pages.
The Journal of Biological Chemistry, Perception of the *Arabidopsis* Danger Signal Peptide 1 Involves the Pattern Recognition Receptor AtPEPR1 and Its Close Homologue AtPEPR2, Krol et al., dated Apr. 30, 2010, in 9 pages.
Springer, Molecular Genetics of Rice Root Development, Rebouillat et al., dated Jul. 9, 2008, in 20 pages.
PNAS, Molecular genetic framework for protophloem formation, Rodriquez-Villalon et al., dated Apr. 22, 2014, in 6 pages.
The Company of Biologists, Primary root protophloem differentiation requires balanced phosphatidylinositol-4,5-biphosphate levels and systemically affects root branching, Rodriguez-Villalon et al. dated Oct. 3, 2014, in 10 pages.
Current Biology, A Signaling Module Controlling the Stem Cell Niche in *Arabidopsis* Root Meristems, Stahl et al., dated Jun. 9, 2009, in 6 pages.
China Academic Journal Electronic Publishing House, Construction of an expression vector of GP-C CTL epitope, Wang et al., dated 2009, in 3 pages.
PNAS, Plant CLE peptides from two distinct functional classes synergistically induce division of vascular cells, Whiford et al., dated Nov. 25, 2008, in 6 pages.
Development Cell, GOLVEN Secretory Peptides Regulate Auxin Carrier Turnover during Plant Gravitropic Responses, Whitford et al., dated Mar. 13, 2012, in 8 pages.

* cited by examiner

A

MGEKERRLRVEGWMGRTEMIDRRRQRLHSGERERRLCVRKRMGSSDFDRG
ARFGGVDDGRLGEGTKRCEEMVGAIWDVGFERDNPDRSTRNEDVNISW

SEQUENCE LISTING

```
<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Amino acid sequence of PEP1

<400> SEQUENCE: 1

Ser Asp Phe Asp Arg
1               5

<210> SEQ ID NO 2
<211> LENGTH: 98
<212> TYPE: PRT
<213> ORGANISM: Artificial Sequence
<220> FEATURE:
<223> OTHER INFORMATION: Amino acid of the precursor protein of PEP1

<400> SEQUENCE: 2

Met Gly Glu Lys Glu Arg Arg Leu Arg Val Glu Gly Trp Met Gly Arg
1               5                   10                  15

Thr Glu Met Ile Asp Arg Arg Arg Gln Arg Leu His Ser Gly Glu Arg
                20                  25                  30

Glu Arg Arg Leu Cys Val Arg Lys Arg Met Gly Ser Ser Asp Phe Asp
            35                  40                  45

Arg Gly Ala Arg Phe Gly Gly Val Asp Asp Gly Arg Leu Gly Glu Gly
        50                  55                  60

Thr Lys Arg Cys Glu Glu Met Val Gly Ala Ile Trp Asp Val Gly Phe
65                  70                  75                  80

Glu Arg Asp Asn Pro Asp Arg Ser Thr Arg Asn Glu Asp Val Asn Ile
                85                  90                  95

Ser Trp

<210> SEQ ID NO 3
<211> LENGTH: 297
<212> TYPE: DNA
<213> ORGANISM: Artificial Sequence
<220> FEATURE:
<223> OTHER INFORMATION: DNA sequence of the coding region of OsPEP1

<400> SEQUENCE: 3
atgggagaga aggagcggag attgcgcgtg gagggatgga tgggcgcac ggagatgatc      60 gatcggcggc ggcaacggct gcactcggga gagagggagc gcagattgtg cgtgaggaaa    120
cggatgggaa gcagcgattt cgatcgaggg gcgcgatttg ggggcgtgga tgacgggaga    180
ctgggagagg ggacgaagcg gtgtgaggag atggtggag cgatttggga cgttggattc    240
```

```
gagcgagaca atcctgaccg atcaacgagg aatgaggatg taaacatcag ttggtga      297
```

```
<210> SEQ ID NO 4
<211> LENGTH: 5
<212> TYPE: PRT
<213> ORGANISM: Artificial Sequence
<220> FEATURE:
<223> OTHER INFORMATION: Amino acid sequence of the Poly-Arg tag

<400> SEQUENCE: 4

Arg Arg Arg Arg Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Amino acid sequence of the Poly-His tag

<400> SEQUENCE: 5

His His His His His His
1               5

<210> SEQ ID NO 6
<211> LENGTH: 8
<212> TYPE: PRT
<213> ORGANISM: Artificial Sequence
<220> FEATURE:
<223> OTHER INFORMATION: Amino acid sequence of the FLAG tag

<400> SEQUENCE: 6

Asp Tyr Lys Asp Asp Asp Asp Lys
1               5

<210> SEQ ID NO 7
<211> LENGTH: 8
<212> TYPE: PRT
<213> ORGANISM: Artificial Sequence
<220> FEATURE:
<223> OTHER INFORMATION: Amino acid sequence of the Strep-tag II

<400> SEQUENCE: 7

Trp Ser His Pro Gln Phe Glu Lys
1               5

<210> SEQ ID NO 8
<211> LENGTH: 10
<212> TYPE: PRT
<213> ORGANISM: Artificial Sequence
<220> FEATURE:
<223> OTHER INFORMATION: Amino acid sequence of the c-myc tag

<400> SEQUENCE: 8

Glu Gln Lys Leu Ile Ser Glu Glu Asp Leu
1               5                   10

<210> SEQ ID NO 9
<211> LENGTH: 20
<212> TYPE: DNA
<213> ORGANISM: Artificial Sequence
<220> FEATURE:
<223> OTHER INFORMATION: Primer for OsPEP1

<400> SEQUENCE: 9
ggcgtggatg acgggagact                                              20
```

```
<210> SEQ ID NO 10
<211> LENGTH: 20
<212> TYPE: DNA
<213> ORGANISM: Artificial Sequence
<220> FEATURE:
<223> OTHER INFORMATION: Primer for OsPEP1

<400> SEQUENCE: 10
tacatcctca ttcctcgttg                                               20

<210> SEQ ID NO 11
<211> LENGTH: 38
<212> TYPE: DNA
<213> ORGANISM: Artificial Sequence
<220> FEATURE:
<223> OTHER INFORMATION: Primer for the 2kb nucleotide sequence before
      OsPEP1 promoter

<400> SEQUENCE: 11
gcatgcctgc aggtcgacgt ttctcagcta cgcccctg                           38

<210> SEQ ID NO 12
<211> LENGTH: 38
<212> TYPE: DNA
<213> ORGANISM: Artificial Sequence
<220> FEATURE:
<223> OTHER INFORMATION: Primer for the 2kb nucleotide sequence before
      OsPEP1 promoter

<400> SEQUENCE: 12
ccatggtacc gtggatcccc ggagcgcagc cgtcgtct                           38

<210> SEQ ID NO 13
<211> LENGTH: 21
<212> TYPE: DNA
<213> ORGANISM: Artificial Sequence
<220> FEATURE:
<223> OTHER INFORMATION: Primer for the gibberellin-resistant gene

<400> SEQUENCE: 13
atgaaaaagc ctgaactcac c                                             21

<210> SEQ ID NO 14
<211> LENGTH: 21
<212> TYPE: DNA
<213> ORGANISM: Artificial Sequence
<220> FEATURE:
<223> OTHER INFORMATION: Primer for the gibberellin-resistant gene

<400> SEQUENCE: 14
ctattccttt gccctcggac g                                             21

<210> SEQ ID NO 15
<211> LENGTH: 35
<212> TYPE: DNA
<213> ORGANISM: Artificial Sequence
<220> FEATURE:
<223> OTHER INFORMATION: Primer for OsPEP1

<400> SEQUENCE: 15 acggggacg agctcatggg agagaaggag cggag                               35

<210> SEQ ID NO 16
<211> LENGTH: 36
<212> TYPE: DNA
<213> ORGANISM: Artificial Sequence
```

```
<220> FEATURE:
<223> OTHER INFORMATION: Primer for OsPEP1

<400> SEQUENCE: 16
gactctagag gatcccaact gatgtttaca tcctca                               36

<210> SEQ ID NO 17
<211> LENGTH: 147
<212> TYPE: DNA
<213> ORGANISM: Artificial Sequence
<220> FEATURE:
<223> OTHER INFORMATION: partial DNA sequence of OsPEP1

<400> SEQUENCE: 17
actcgggaga gagggagcgc agattgtgcg tgaggaaacg gatgggaagc agcgatttcg    60
atcgaggggc gcgatttggg ggcgtggatg acgggagact gggagagggg acgaagcggt  120
gtgaggagat ggtgggagcg atttggg                                       147

<210> SEQ ID NO 18
<211> LENGTH: 20
<212> TYPE: DNA
<213> ORGANISM: Artificial Sequence
<220> FEATURE:
<223> OTHER INFORMATION: Primer for partial DNA sequence of OsPEP1

<400> SEQUENCE: 18
actcgggaga gagggagcgc                                                20

<210> SEQ ID NO 19
<211> LENGTH: 20
<212> TYPE: DNA
<213> ORGANISM: Artificial Sequence
<220> FEATURE:
<223> OTHER INFORMATION: Primer for partial DNA sequence of OsPEP1

<400> SEQUENCE: 19
cccaaatcgc tcccaccatc                                                20
```

ROOT-SECRETED PEPTIDE PEP1 IN RICE AND GENE ENCODING THE SAME AND USE THEREOF

CROSS REFERENCE TO RELATED APPLICATION

This patent application is the US national phase entry of international patent application PCT/CN2021/112192, filed Aug. 12, 2021, which claims the benefit and priority of Chinese Patent Application No. 202110194477.8, entitled "Root-Secreted Peptide PEP1 in Rice and Gene Encoding the Same and Use Thereof" filed on Feb. 20, 2021, the disclosure of which is incorporated by reference herein in its entirety as part of the present application.

TECHNICAL FIELD

The disclosure relates to the field of biotechnology, in particular to the use of a plant root-secreted peptide and a gene encoding the same in regulation of the growth and development of plant roots.

BACKGROUND ART

Roots are important underground organs of plants, which not only support plants, but also take up nutrients, water and other substances from soil for plant growth and development. In addition, the root system of plants also monitor various signal molecules in the soil, such as moisture content, nutrient levels, and plant hormones, to improve plant adaptability (Meng et al. 2019). Plant roots are mainly divided into two categories, tap root system and fibrous root system. Rice is a monocotyledonous model plant with a fibrous root system consisting mainly of seminal root, adventitious root, and lateral root and root hair (Rebouillat et al. 2009; Coudert et al. 2010). Studies have shown that a high root-to-shoot ratio and a well-developed root system can improve rice drought resistance and yield (Fukai et al. 1995; Gowda et al. 2011). Previous studies have shown that the growth and development of rice roots are strictly regulated by exogenous signals and endogenous genetic programs (Benfey et al. 2012; Orman-Ligeza et al. 2013).

Previous studies have shown that peptides act as exogenous signal molecules to regulate root development in *Arabidopsis* (Oh et al., 2018). Exogenous application of synthetic peptide root meristem growth factor 1 (RGF1) restores the apical meristem-deficient phenotype in tpst-1 mutants, suggesting that RGF1 is required for the maintenance of apical stem cells (Matsuzaki et al. 2010). Further genetic analysis reveals that RGF/GLV controls the abundance and trafficking dynamics of the auxin efflux carrier PINFORMED 2 in root meristem through a post-transcriptional regulatory mechanism, thereby regulating the size of plant root apical meristem (Whitford et al. 2012). The size of plant root tip meristem is also regulated by the CLE (CLAVATA 3 (CLV3)/EMBRYO SURROUNDING REGION (ESR)-related) family of peptides. There are 32 genes encoding the CLE peptides in *Arabidopsis*, and those peptides can be divided into two groups: A-type CLE and B-type CLE. Type A CLE peptides play roles in root meristem development, while type B CLE peptides are involved in root vascular bundle development (Cock and McCormick 2001; Whitford et al. 2008). For example, the type A CLE peptide CLE40 is required for columnar cell differentiation, and the loss-of-function mutant cle40 exhibits an irregularly shaped root tip due to the delayed differentiation of columella cells, thereby exhibiting a short root phenotype (Stahl et al. 2009). Other CLE peptides such as CLE26, CLE40 and CLE45 control primary root growth by regulating primary epithelium formation during vascular bundle development (Depuydt et al. 2013; Rodriguez-Villalon et al. 2014; Rodriguez-Villalon et al. 2015; Hazak et al. 2017). In addition, the tyrosine sulfated peptides PHYTO-SULFOKINE (PSK) and PLANT PEPTIDE CONTAINING SULFATED TYROSINE 1 (PSY1) can promote primary root growth by regulating cell expansion in the elongation/meristematic zone (Amano et al. 2007; Kwezi et al. 2011; Hartmannet et al. 2014; Ladwiget et al. 2015). The peptide CASPARIAN STRIP INTEGRITY FACTOR 1 (CIF1) is essential for casparian strip formation, as CIF1 loss-of-function mutants exhibit severe growth retardation at high iron concentrations, while these defects can be fully recovered by exogenous application of CIF1 peptide (Nakayama et al. 2017).

Compared with *Arabidopsis*, the mechanism by which peptides regulate rice root growth and development is still unclear. Therefore, it is very important and necessary to isolate and identify peptides related to rice root growth and development, and to determine genes encoding these peptides to further fully understand the mechanism of root development of rice and other monocots, and to obtain desired genes for the breeding of new rice cultivars.

REFERENCES

Amano Y, Tsubouchi H, Shinohara H et al (2007) Tyrosine-sulfated glycopeptide involved in cellular proliferation and expansion in *Arabidopsis*. Proc. Natl. Acad. Sci. U.S.A 104, 18333-18338.

Benfey P N (2012) Toward a Systems Analysis of the Root. Cold Spring Harbor Symposia on Quantitative Biology 77, 91.

Cock J and McCormick S (2001) A large family of genes that share homology with CLAVATA3. Plant Physiol. 126, 939-942.

Coudert Y, Bès M, Le T V et al (2011) Transcript profiling of crown rootless 1 mutant stem base reveals new elements associated with crown root development in rice. BMC Genomics 12, 1-12.

Coudert Y, Perin C, Courtois B et al (2010) Genetic control of root development in rice, the model cereal. Trends Plant Sci. 15, 219-226.

Depuydt S, Rodriguez-Villalon A, Santuari L et al (2013) Suppression of *Arabidopsis* protophloem differentiation and root meristem growth by CLE45 requires the receptor-like kinase BAM3. Proc. Natl. Acad. Sci. U.S.A 110, 7074-7079.

Fukai S, Cooper M (1995) Development of drought resistant cultivars using physio-morphological traits in rice. Field Crops Res. 40, 67-87.

Hartmann J, Fischer C, Dietrich P et al (2014) Kinase activity and calmodulin binding are essential for growth signaling by the phytosulfokine receptor PSKR1. Plant J. 78, 192-202.

Hazak O, Brandt B, Cattaneo P et al (2017) Perception of root-active CLE peptides requires CORYNE function in the phloem vasculature. EMBO Rep. 18, 1367-1381.

Kwezi L, Ruzvidzo O, Wheeler J I et al (2011) The phytosulfokine (PSK) receptor is capable of guanylate cyclase activity and enabling cyclicGMP-dependent signaling in plants. J. Biol. Chem. 286, 22580-22588.

Ladwig F, Dahlke R I, Stührwohldt N et al (2015) Phytosulfokine regulates growth in *Arabidopsis* through a response module at the plasma membrane that includes CYCLIC NUCLEOTIDE-GATED CHANNEL17, H+-ATPase, and BAK1. Plant Cell 27, 1718-1729.

Lv Q, Zhong Y, Wang Y et al (2014) SPX4 negatively regulates phosphate signaling and homeostasis through its interaction with PHR2 in rice. Plant Cell 26, 1586-1597.

Matsuzaki Y, Ogawa-Ohnishi M, Mori A et al (2010) Secreted peptide signals required for maintenance of root stem cell niche in *Arabidopsis*. Science 329, 1065-1067.

Meng F, Xiang D, Zhu J et al (2019) Molecular mechanisms of root development in rice. Rice 12, 1.

Nakayama T, Shinohara H, Tanaka M et al (2017) A peptide hormone required for Casparian strip diffusion barrier formation in *Arabidopsis* roots. Science 355, 284-286.

Orman-Ligeza B, Parizot B, Gantet P P et al (2013) Post-embryonic root organogenesis in cereals: branching out from model plants. Trends Plant Sci. 18, 459-467.

Rebouillat J, Dievart A, Verdeil J L et al (2009) Molecular genetics of rice root development. Rice 2, 15-34.

Rodriguez-Villalon A, Gujas B, Kang Y H et al (2014) Molecular genetic framework for protophloem formation. Proc. Natl. Acad. Sci. U.S.A 111, 11551-11556.

Rodriguez-Villalon A, Gujas B, van Wijk R et al (2015) Primary root protophloem differentiation requires balanced phosphatidylinositol-4,5-biphosphate levels and systemically affects root branching. Development 142, 1437-1446.

Stahl Y, Wink R H, Ingram G C et al (2009) A signaling module controlling the stem cell niche in *Arabidopsis* root meristems. Curr. Biol. 19, 909-914.

Wang W J, Li C Y, Li M S (2019) Construction of an expression vector of GPC-3 CTL epitope. Journal of Southern Medical University 29, 1548-1550.

Whitford R, Fernandez A, De Groodt R et al (2008) Plant CLE peptides from two distinct functional classes synergistically induce division of vascular cells. Proc. Natl. Acad. Sci. U.S.A 105, 18625-18630.

Whitford R, Fernandez A, Tejos R et al. (2012) GOLVEN secretory peptides regulate auxin carrier turnover during plant gravitropic responses. Dev. Cell 22, 678-685.

SUMMARY

The technical problem to be solved by the present disclosure is to provide a peptide for regulating plant root development and a gene encoding the same and use thereof.

In order to solve the technical problem, the present disclosure provides a use of a peptide for regulating plant root development in treatment of a plant, in which a root length of the plant is shortened or lengthened upon the treatment;
the peptide is selected from the group consisting of:
a peptide having the amino acid sequence set forth in SEQ ID NO: 1; and
a peptide derived from the peptide having the amino acid sequence of set forth in SEQ ID NO: 1 with a substitution and/or a deletion and/or an addition of one or more amino acid residues thereof, and being related to regulation of plant root development.

In some embodiments of the use of the peptide in regulation of plant root development in the present disclosure:
a precursor protein of the peptide is selected from the group consisting of a precursor protein having the amino acid sequence set forth in SEQ ID NO: 2; and
a precursor protein derived from the precursor protein having the amino acid sequence set forth in SEQ ID NO: 2 with a substitution and/or a deletion and/or an addition of one or more amino acid residues thereof, and being related to plant development;

The present disclosure provides a use of a gene for regulating plant root development in constructing a transgenic plant, in which a root length of the transgenic plant is shortened or lengthened upon treatment;
the gene is selected from the group consisting of:
a gene with a coding region having the nucleotide sequence set forth in SEQ ID NO: 3; and
a gene derived from the gene with a coding region having the nucleotide sequence set forth in SEQ ID NO: 3 with a substitution and/or a deletion and/or an addition of one or more nucleotides thereof, and being related to regulation of plant root development.

In some embodiments of the use of the gene for regulating plant root development in the present disclosure, the plant is rice.

In some embodiments of the use of the gene in the present disclosure,
a plant is treated with the peptide of different concentrations to obtain a plant with shortened or lengthened root length;
in some embodiments of the use of the gene in the present disclosure,
a recombinant expression vector I is introduced into a target plant to obtain a transgenic plant with a shortened root length;
a DNA molecule set forth in SEQ ID NO:3 is inserted into a multiple cloning site of a plasmid pCAMBIA1300 to obtain a recombinant-expression-vector-I-OsPEP1 overexpression vector.

In some embodiments of the use of the gene in the present disclosure,
a recombinant expression vector II is introduced into a target plant to obtain a transgenic plant with a shortened root length;
a DNA fragment of the gene set forth in SEQ ID NO: 3 is ligated to a transition vector pBSSK-in in sense and antisense orientations, and then inserted into a plasmid pCAMBIA1300 to obtain a recombinant-expression-vector-II-OsPEP1 RNAi expression vector.

The technical scheme of the present disclosure is as follows:

The peptide PEP1, the precursor protein, and the gene encoding the same provided by the present disclosure are from the *japonica* rice Xiushui 134 (*Oryza sativa* L. ssp. *Japonica* cv. Xiushui134), in which the peptide is a peptide selected from the group consisting of the following (a) and (b), and the precursor protein, or the gene encoding the same are selected from the group consisting of (a), (b), (c), (d), (e) and (f):
(a) a peptide having the amino acid sequence set forth in SEQ ID NO: 1;
(b) a peptide derived from the peptide having the amino acid sequence set forth in SEQ ID NO: 1 with a substitution and/or a deletion and/or an addition of one or more amino acid residues and being related to plant development;
(c) a precursor protein having the amino acid sequence set forth in SEQ ID NO: 2;
(d) a precursor protein derived from the precursor protein having the amino acid sequence set forth in SEQ ID NO: 2 with a substitution and/or a deletion and/or an addition of one or more amino acid residues and being related to plant development;
(e) a gene having the nucleotide sequence set forth in SEQ ID NO:3;

(f) a gene derived from the gene having the nucleotide sequence set forth in SEQ ID NO: 3 with a substitution and/or a deletion and/or an addition of one or more nucleotides and being related to plant development;

The plant development is referred to a plant root length trait.

To facilitate purification of PEP1 in (a), tags including but not limited to those set forth in Table 1 are attached to an amino terminus or carboxyl terminus of the peptide having the amino acid sequence set forth in SEQ ID NO: 1.

TABLE 1

Sequence of the tags

| Tag | Residue | Sequence |
| --- | --- | --- |
| Poly-Arg | 5-6 (usually 5) | RRRRR (SEQ ID NO: 4) |
| Poly-His | 2-10 (usually 6) | HHHHHH (SEQ ID NO: 5) |
| FLAG | 8 | DYKDDDDK (SEQ ID NO: 6) |
| Strep-tag II | 8 | WSHPQFEK (SEQ ID NO: 7) |
| c-myc | 10 | EQKLISEEDL (SEQ ID NO: 8) |

PEP1 in (a) is artificially synthesized, or the gene encoding PEP1 is synthesized first, and then biologically expressed. The gene encoding PEP1 in (a) is obtained by deleting the codons of one or more amino acid residues in the DNA sequence set forth in SEQ ID NO: 3, and/or making one or more base pairs missense. The sequence encoding the peptide is obtained by mutating, and/or ligating the tags set forth in Table 1 at its 5' end and/or 3' end.

A gene encoding the protein also belongs to the protection scope of the present disclosure.

The gene OsPEP1 encoding the precursor protein is selected from a DNA molecule of the following 1) or 2) or 3):

1) a DNA molecule having the coding sequence set forth in SEQ ID NO:3, that is, coding region of the gene having the nucleotide sequence set forth in SEQ ID NO:3;
2) a DNA molecule that hybridizes with a DNA sequence defined in 1) and encodes a protein of the same function under stringent conditions;
3) a DNA molecule that is more than 90% identical to the DNA sequence defined in 1) or 2) and encodes a protein of the same function.

A recombinant expression vector, an expression cassette, a transgenic cell line or a recombinant bacterium containing the gene or antisense gene thereof all fall within the protection scope of the present disclosure.

The recombinant expression vector containing the gene OsPEP1 is constructed with an existing plant expression vector.

The plant expression vector includes, but is not limited to, for example, a binary *Agrobacterium* vector and a vector that is used for plant microprojectile bombardment, and the like. The plant expression vector may also contain the 3' untranslated region of an exogenous gene, ie, a polyadenylation signal and any other DNA fragments involved in mRNA processing or gene expression. The polyadenylation signal guides the addition of polyadenylic acid to the 3' terminus of the mRNA precursor, including but not limited to, for example, 3' terminus of a *Agrobacterium* crown gall-inducing (Ti) plasmid gene (such as nopaline synthase Nos gene), a plant gene (such as a soybean storage protein gene) 3'-terminal transcribed untranslated regions, which has similar functions.

When OsPEP1 is used to construct a plant recombinant expression vector, any strong promoter or constitutive promoter can be added before the transcription initiation nucleotides, including but not limited to, for example, a cauliflower mosaic virus (CAMV) 35S promoter, and a Maize ubiquitin promoter, which can be used alone or in combination with other plant promoters; in addition, when the gene of the present disclosure is used for construction of a plant expression vector, an enhancer can also be used, including a translation enhancer or a transcription enhancer. These enhancer regions may be located near ATG start codons or adjacent region start codons, etc., but must share the same reading frame with the coding sequence to ensure the correct translation of the entire sequence. The translation control signals and start codons may be derived from a wide variety of sources, either natural or synthetic. Translation initiation regions can be from transcription initiation regions or structural genes.

In order to facilitate the identification and screening of transgenic plant cells or plants, the plant expression vector used may be processed, such as adding, including but not limited to, genes that are expressed in plants and encode enzymes or luminance compounds that produce color changes (GUS gene, luciferase gene, etc.), antibiotic-resistant markers (gentamicin marker, kanamycin marker, etc.) or chemical-resistant marker genes (e.g., herbicide-resistant genes), etc. In consideration of the security of transgenic plants, the transformed plants can be directly screened under stress without adding any selectable marker gene.

The recombinant expression vector may be the following (I) or (II):
(I) a recombinant expression vector containing the gene obtained by inserting the DNA molecule as set forth in SEQ ID NO:3 into a multiple cloning site of a plasmid pCAMBIA1300;
(II) a recombinant expression vector obtained by ligating a DNA fragment as set forth in SEQ ID NO: 3 to a transition vector pBSSK-in and conducting insertion into a plasmid pCAMBIA1300 through forward and reverse ligation;

The plasmids pCAMBIA1300 and pBSSK-in in (I) or (II) are both obtained by engineering (already published).

The present disclosure also claims a method for cultivating a transgenic plant, including introducing the gene or gene fragment into a target plant by forward and reverse ligation to the transition vector pBSSK-in, in which the transgenic plant is a transgenic plant with altered root length as compared to that of the target plant.

Using any vector that can induce the expression of exogenous genes in plants, the OsPEP1 gene or gene fragment provided by the present disclosure is ligated to the transition vector pBSSK-in in sense and antisense orientations and then introduced into plant cells, so that a transgenic cell line and a transgenic plant with altered root length are obtained. Expression vectors carrying the whole or partial OsPEP1 gene that is forwardly and reversely ligated can be used to transform plant cells or tissue by conventional biological methods such as Ti plasmid, Ri plasmid, plant virus vector, direct DNA transformation, microinjection, electrical conductivity, and *Agrobacterium*-mediated method, and the transformed plant tissue is grown into a plant. The transformed plant host may be a poaceae plant, such as rice (e.g., Xiushui 134).

When a transgenic plant whose root length is longer or shorter than that of the target plant is to be cultivated, the method is to introduce (I) the recombinant expression vector into the target plant and a transgenic plant with shortened roots is obtained. When a transgenic plant whose root length is shorter than that of the target plant is to be cultivated, the method is to introduce the recombinant expression vector (II) into the target plant and a transgenic plant with shortened roots is obtained.

The present disclosure discovers a new rice root secreted peptide PEP1 and gene OsPEP1 encoding PEP1, and obtains a recombinant expression vector containing the gene or a partial fragment of the gene that is ligated to the transition vector pBSSK-in in sense and antisense orientations. The target plant is transformed with the recombinant vector, so that a transgenic plant with altered root length is obtained. Therefore, OsPEP1 can be used as a potential molecular breeding tool to improve plant yield by improving root length of plants.

In conclusion, the present disclosure isolates and identifies a peptide PEP1 that regulates rice root growth and development, and determines the gene OsPEP1 (LOC_Os11g09560) encoding PEP1 and precursor protein OsPEP1. That is, the present disclosure isolates and identifies a peptide PEP1 associated with plant root growth and development and gene OsPEP1 encoding PEP1. Exogenous application of PEP1 inhibits root growth and development. And a recombinant expression vector containing the gene encoding the peptide or part of the DNA of the gene is obtained, and a plant transformed with the recombinant expression vector can obtain a transgenic plant with altered root growth and development. Therefore, the peptide may be used as a plant growth regulator, and the gene encoding the same and its precursor protein may be used as a potential molecular breeding target for crop improvement, such as improving crop yield by regulating crop root growth and development.

BRIEF DESCRIPTION OF THE DRAWINGS

The specific embodiments of the present disclosure will be further described in detail below with reference to the accompanying drawings.

A is the amino acid sequence of the protein encoded by the gene OsPEP1 (MGEKERRLRVEGWMGRTEMI-DRRRQRLHSGERERRLCVRKRMGSSDFDRGA RFGGVDDGRLGEGTKRCEEMVGAIWDVGFERD-NPDRSTRNEDVNISW, SEQ ID NO: 2), the peptide PEP1 with 5 amino acid residues is underlined;

B illustrates LC-MS analysis of the peptide secreted by the roots of wild-type rice plants;

C illustrates LC-MS/MS identification of Ser-Asp-Phe-Asp-Arg (PEP1) (SEQ ID NO: 1), a wild-type rice plant root secreted peptide, with a retention time of 12.25 minutes;

D illustrates LC-MS analysis of root secreted peptide of a transgenic rice plant overexpressing LOC_Os11g09560;

E illustrates LC-MS/MS identification of the root secreted peptide Ser-Asp-Phe-Asp-Arg (PEP1) (SEQ ID NO: 1) of a transgenic rice plant overexpressing LOC_Os11g09560, with a retention time of 12.26 minutes.

Figure 2:
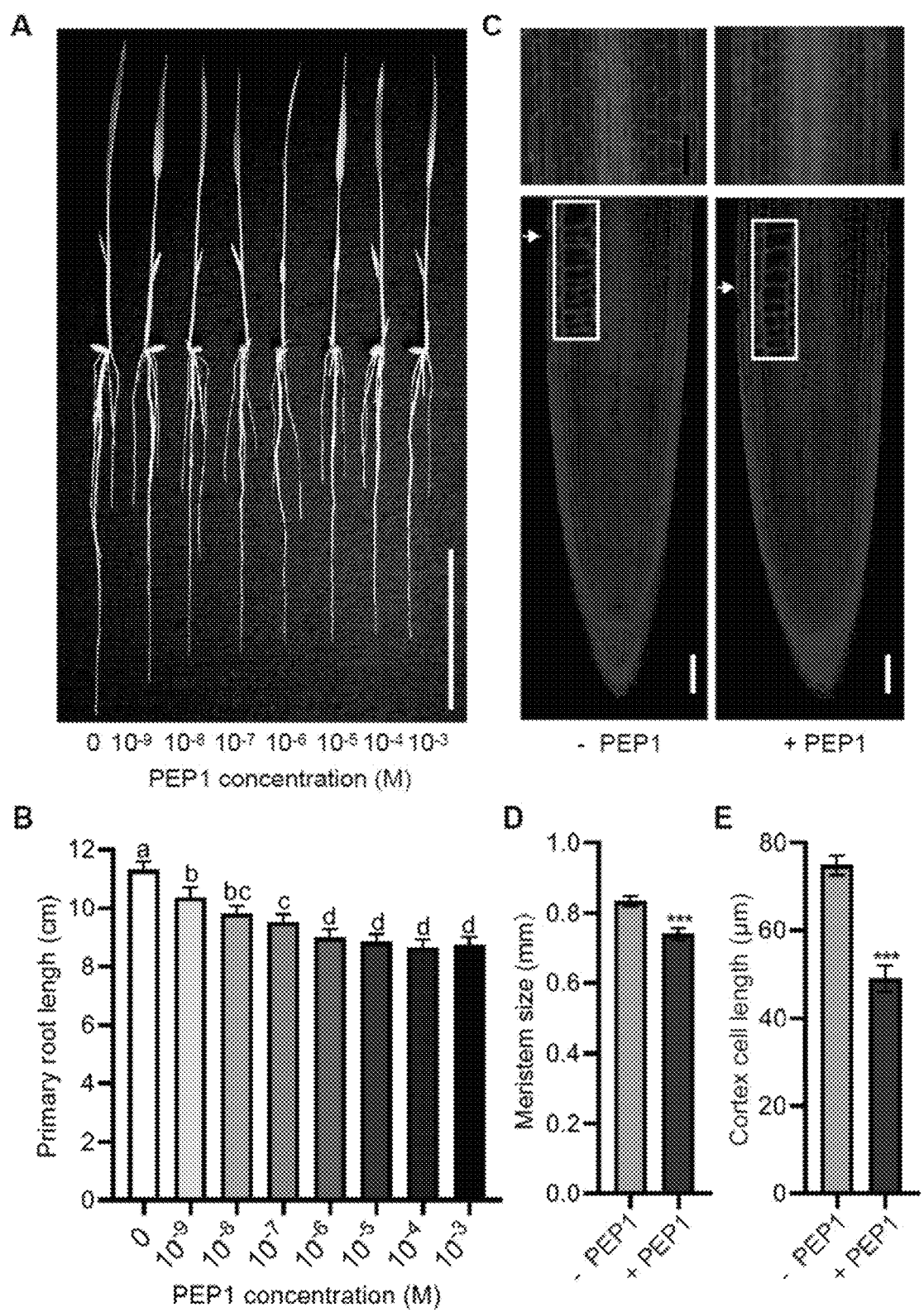
Figure 3:
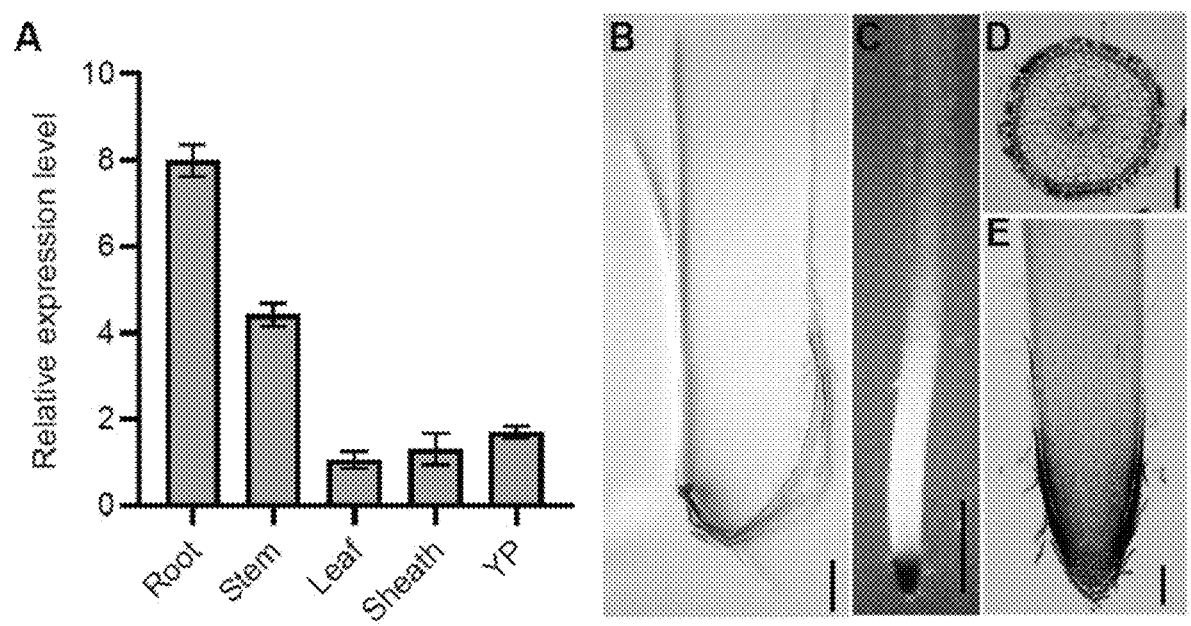

FIG. 2 illustrates the functional analysis of root secreted peptide PEP1 in Example 1;

A shows the phenotype of wild-type plants treated with different concentrations of PEP1 for 7 days, with a scale bar of 5 cm;

B shows statistics of the primary root length of wild-type plants treated with different concentrations of PEP1 for 7 days, Data are shown as Mean±SD (n≥15 independent seedlings, three biological replicates). Different letters indicate significant differences (P<0.01, ANOVA, LSD test);

C shows the longitudinal section phenotype of root apical elongation zone (upper left) and meristem (lower left) of wild-type plants without PEP1 (−PEP1) treatment or that of the elongation zone (top right) and meristem (bottom right) treated with 106 M PEP1 (+PEP1) for 2 days. Bar=100 μm;

D is the statistics of the length of the meristem in panel C, and data are shown as Mean±SD (n≥15 independent seedlings). ***Significant difference from WT (P<0.001, Student's t-test);

E is the statistics of cell length in the elongation zone in C, and data are shown as Mean±SD (n≥15 independent seedlings). ***Significant difference from WT (P<0.001, Student's t-test);

FIG. 3 is the expression profile of gene OsPEP1 in Example 2;

A shows expression level of the gene OsPEP1 detected by qRT-PCR in rice roots, stems, leaves, and young ears, which were sampled from 7-day-old rice seedlings;

B shows GUS staining of the Pro$_{OsPEP1}$::GUS transgenic plant at the age of 7 days. Bar=1 cm;

C shows GUS staining of the primary root of the 2-day-old Pro$_{OsPEP1}$::GUS transgenic plant. Bar=0.1 cm;

D shows the cross-section GUS staining of the primary root elongation zone in C, with a scale bar of 100 μm;

E is the longitudinal section GUS staining of the primary root meristem in C, with a scale bar of 100 μm.

Figure 4:
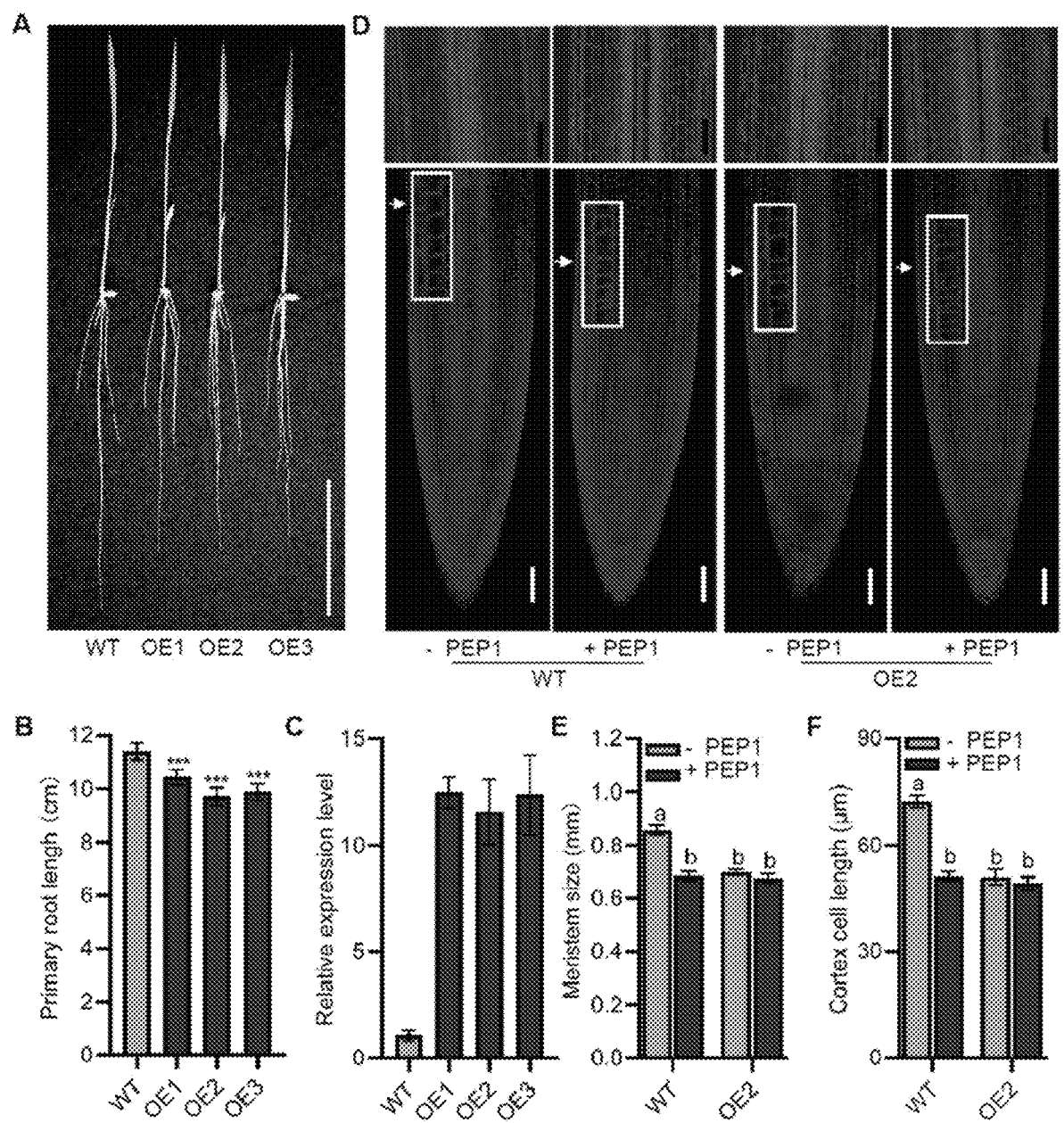

FIG. 4 is the phenotypic analysis of transgenic plants overexpressing OsPEP1 in Example 2;

A shows the phenotype of 7-day-old seedlings of WT and plant lines OE1, OE2 and OE3 overexpressing OsPEP1. Bar=5 cm;

B is the statistics of the primary root length of the corresponding plants indicated in A. Data are means±SD (n≥15 independent seedlings). ***Significant difference from WT (P<0.001, Student's t-test);

C shows expression level of the gene OsPEP1 detected by qRT-PCR in the corresponding plants indicated in A. Data are means±SD (n=3 biological replicates);

D shows longitudinal phenotype of the root tip elongation zone (top) and meristem (bottom) of the wild-type WT and that of the transgenic plant OE2 overexpressing OsPEP1 treated with $10^{-6}$ M PEP1 for 2 days. Bar=100 μm;

E is the statistics of the apical meristem length indicated in D. Data are means±SD (n≥15 independent seedlings, three biological replicates). Different letters indicate significant differences (P<0.01, ANOVA, LSD test);

F is the statistics of the cell length in the elongation zone indicated in D. Data are means±SD (n≥15 independent seedlings, three biological replicates). Different letters indicate significant differences (P<0.01, ANOVA, LSD test).

Figure 5:
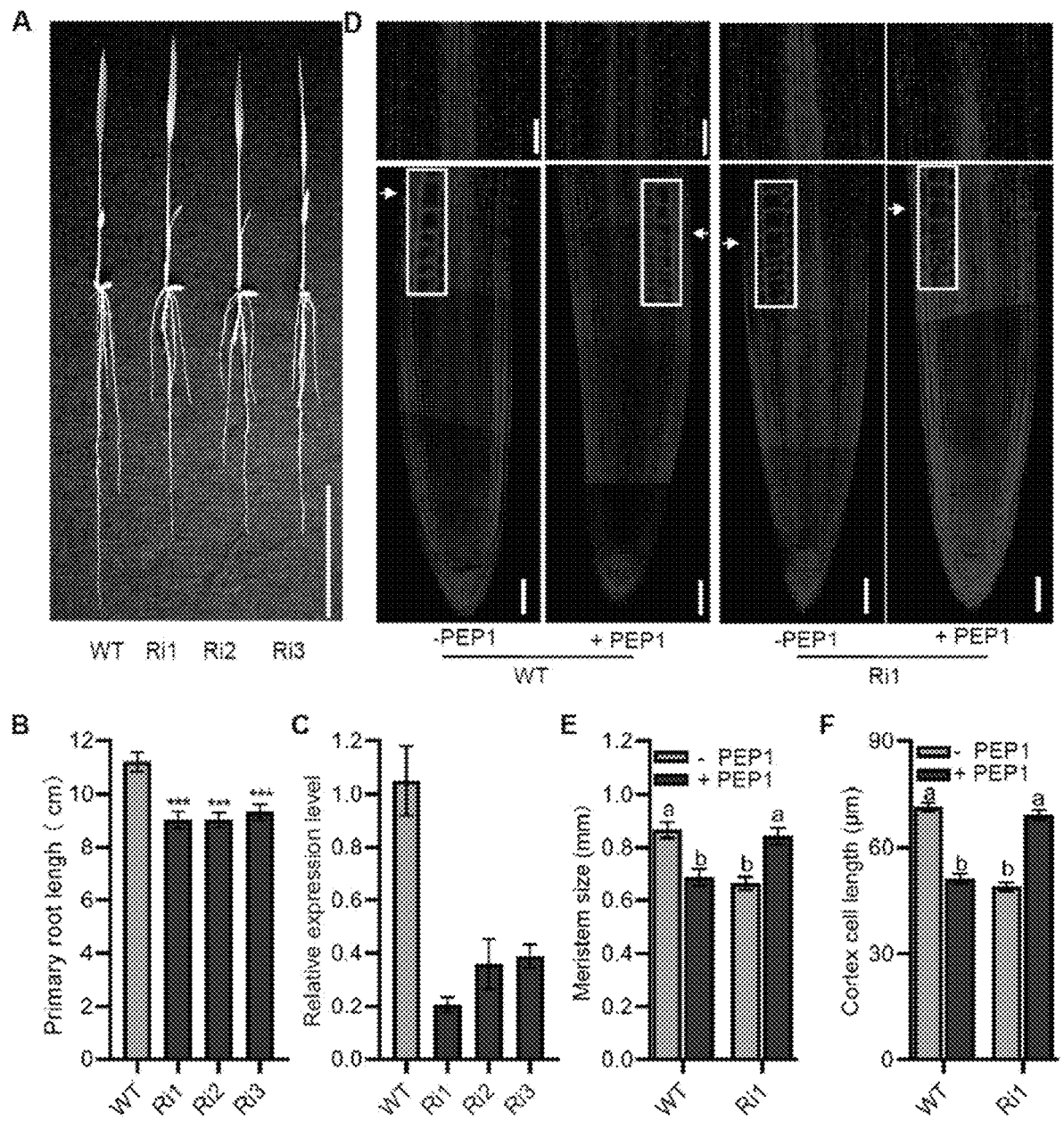

FIG. 5 is the phenotypic analysis of transgenic plants underexpressing OsPEP1 in Example 2;

A shows the phenotype of 7-day-old seedlings of WT and that of plant lines Ri1, Ri2 and Ri3 interfering OsPEP1. Bar=5 cm;

B is the statistics of the primary root length of the corresponding plants indicated in A. Data are means±SD (n≥15 independent seedlings). ***Significant difference from WT (P<0.001, Student's t-test);

C shows the expression level of the gene OsPEP1 detected by qRT-PCR in the corresponding plants indicated in A. Data are means±SD (n=3 biological replicates);

D is the longitudinal phenotype of the root tip elongation zone (top) and meristem (bottom) of the wild-type WT and the transgenic plant Ri2 overexpressing OsPEP1 treated with $10^{-6}$ M PEP1 for 2 days. Bar=100 μm;

E is the statistics of the apical meristem length indicated in D. Data are means±SD (n≥15 independent seedlings, three biological replicates). Different letters indicate significant differences (P<0.01, ANOVA, LSD test);

F is the statistics of cell length in the elongation zone indicated in D. Data are means±SD (n≥15 independent seedlings, three biological replicates). Different letters indicate significant differences (P<0.01, ANOVA, LSD test).

DETAILED DESCRIPTION OF THE EMBODIMENTS

The present disclosure is further described below in conjunction with specific examples, but the protection scope of the present disclosure is not limited to this.

The composition of the hydroponic medium is shown in Table 2.

TABLE 2

Composition of hydroponic culture medium

| Name | Components | MW | Mol | g/L | 10000× | Final (mM) |
|---|---|---|---|---|---|---|
| Stock-1 | MgSO4•7H2O | 246.3 | 0.547 | 134.800 | 10 ml | 0.5470 |
| | (NH4)2SO4 | 132.0 | 0.365 | 48.200 | | 0.3650 |
| Stock-2 | KH2PO4 | 136.1 | 0.182 | 24.800 | 10 ml | 0.1820 |
| Stock-3 | KNO3 | 101.1 | 0.183 | 18.500 | 10 ml | 0.1830 |
| | Ca(NO3)2•4H2O | 236.0 | 0.366 | 86.400 | | 0.3660 |
| Stock-4 | MnCl2•4H2O | 197.9 | 0.005 | 0.990 | 1 ml | 0.0005 |
| | H3BO3 | 61.8 | 0.03 | 1.860 | | 0.0030 |
| | (NH4)6Mo7O24•4H2O | 1235.9 | 0.001 | 1.236 | | 0.0001 |
| | ZnSO4•7H2O | 287.5 | 0.004 | 1.150 | | 0.0004 |
| | CuSO4•5H2O | 249.5 | 0.002 | 0.518 | | 0.0002 |
| Stock-5 | NaFe-EDTA•3H2O | 421.1 | 0.100 | 42.100 | 4 ml | 0.0400 |
| MES | MES | 195.2 | 0.500 | 97.620 | 40 ml | 2.0000 |

The detection results of gene expression levels in the following examples, unless otherwise specified, are all based on the target gene expression level of the wild-type plant Xiushui 134 as 1, and the target gene expression levels of other plants are compared with those of the wild-type plant.

Example 1. Acquisition of Rice Peptide PEP1 and Functional Study Thereof

1. Acquisition of Rice Peptide PEP1 and Gene Encoding the Same
(1). Acquisition of the Root-Secreted Peptide in Rice.

30 plump wild-type rice (Xiushui 134) seeds were treated with 0.5% nitric acid for 16-22 hours to break up the dormancy, and washed with tap water for 2-3 times, and then tap water was added to soak the seeds for germination acceleration in an incubator at 37° C. for two days until sprouting. During this period, the water was changed every morning and evening. Finally, the germinated seeds were sown on the nylon mesh floating on the nutrient solution (hydroponics medium), and cultured in an artificial climate chamber. The culture conditions in the artificial climate chamber were as follows: light for 14 hours, the average day and night temperature was 30° C./22° C., the light intensity was maintained at 200 μmol/m$^2$s$^1$, and the humidity was 60%. After 10 days of culture, the medium was collected for subsequent concentration, extraction and precipitation of root exudates. The specific method is as follows: first, a rotary evaporator was used to concentrate the culture solution (500 ml) obtained in the previous step by 20 fold. Then, 20 ml of chlorophenol containing 1% NEM (N-ethylmorpholine, N-ethylmorpholine) was added and a resulting mixture was shaken for 1 minute at room temperature, centrifuged at 10,000 g for 10 minutes. A resulting organic phase was collected, and 20 times the volume of acetone was added to precipitate overnight at room temperature. Then a resulting mixture was centrifuged at 10000 g for 10 minutes, then a resulting precipitate was collected, washed with acetone for 3-4 times, and then vacuum dried to powder. Finally, the powder was sent to the company (Applied Protein Technology, co., Ltd) to identify 234 rice root-secreted peptides using liquid chromatography tandem mass spectrometry (LP-MS/MS).

(2). Acquisition of Candidate Genes Encoding Rice Root-Secreted Peptides.

Previous study have shown that the products of genes encoding some small signaling peptides (PSK, PSY1, CLV3/CLE) in *Arabidopsis* were cysteine-poor proteins with a length of 70-110 amino acids. Therefore, it is speculated in the present disclosure that if proteins encoded by certain genes in rice have these characteristics, the genes may be candidate genes encoding similar peptides. Based on this speculation, a total of 66,343 protein-coding genes from the Rice Genome Annotation Project rice.plantbiology.msu.edu/index.shtml, March 2017) were downloaded, and then 12,678 protein-coding genes with a length of 50-150 amino acids were retrieved with MICROSOFT WORD® 2003 and EXCEL® 2003. The secreted peptide had a signal peptide sequence at its N-terminus. In the present disclosure, SignalP 4.1 server in the HMM webpage was used for screening and 704 protein-coding genes with a signal peptide at the N-terminus (P≥0.75) were obtained. Finally, EXCEL 2003 was used to exclude protein-encoding genes containing 6 or more cysteines and 416 candidate rice peptide-encoding genes were obtained.

(3). Identification of Rice Root-Secreted Peptide PEP1 and Gene Encoding the Same.

Figure 1:
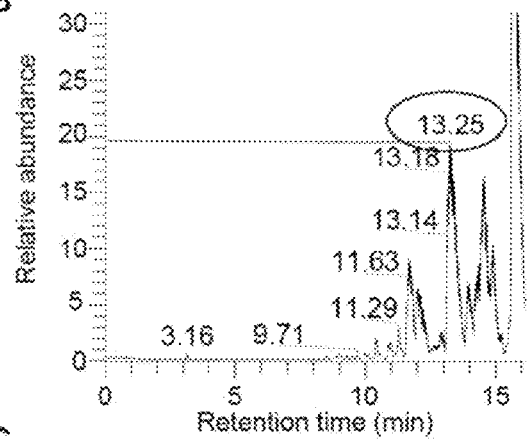
FIG. 1 shows that the gene OsPEP1 (LOC_Os11g09560) in Example 1 encodes a protein containing five amino acids (SDFDR, SEQ ID NO: 1)
Figure 1:
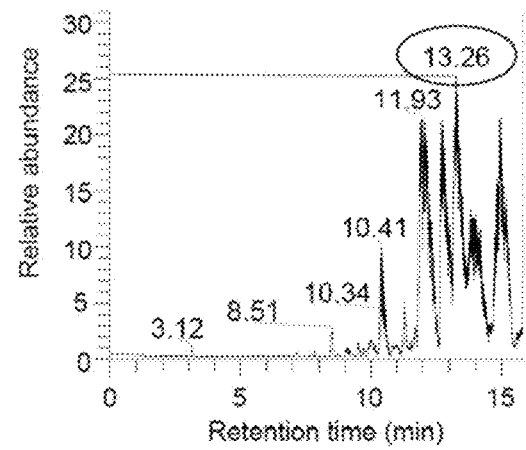
Figure 1:
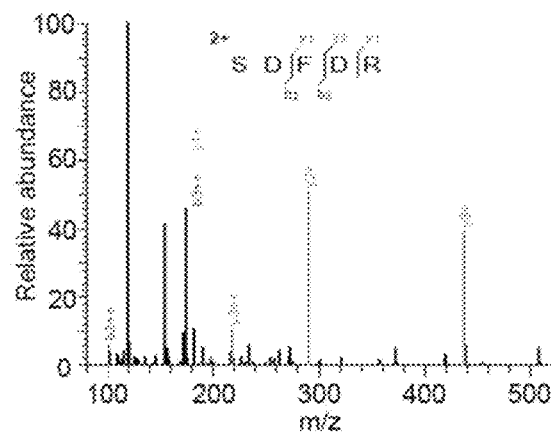

By comparing the 234 root-secreted peptides obtained by method (1) with the 416 putative rice peptide-encoding genes obtained by method (2), a novel peptide (Ser-Asp-Phe-Asp-Arg, SEQ ID NO:1) was identified in the present disclosure and candidate gene encoding the same (LOC_Os11g09560) (A in FIG. 1) was determined. In order to further confirm that LOC_Os11g09560 indeed encodes peptide PEP1, LC-MS/MS was used in the present disclosure to detect the root secretions of the LOC_Os11g09560 overexpressing transgenic plants. The results showed that the peak of this peptide in the root secretions of the LOC_Os11g09560 overexpressing transgenic plants were significantly enhanced (B-E in FIG. 1), indicating that the gene LOC_Os11g09560 indeed encodes peptide PEP1. Thereafter, the peptide (Ser-Asp-Phe-Asp-Arg, SEQ ID NO: 1) was named PEP1, and the gene encoding the LOC_Os11g09560 was named OsPEP1.

2. Functional Study of the PEP1

In the present disclosure, different concentrations of artificially synthetic PEP1 were used to treat rice seedlings (the concentrations were as described in A in FIG. 2, and the treatment started after sowing and lasted for 7 days), and the results showed that exogenous application of PEP1 significantly inhibited rice primary root elongation (A and B in FIG. 2). In order to clarify the cellular basis of the PEP1 inhibitory effect on rice root elongation, we observed the section structure of these rice root tips, and found that after PEP1 treatment, the length of the meristem and cells in the elongation zone of rice root tips were significantly shortened. However, there were no significant changes in the quiescent center (as shown in the meristem of the root section, C-E in FIG. 2).

Example 2. Study on Expression Profile of the Rice Peptide PEP1 Encoding Gene OsPEP1

1. Expression of OsPEP1 in Different Rice Tissues Determined by qRT-PCR

Xiushui 134 rice was used as material, and cultured in normal nutrient solution (hydroponic culture medium) for 7 days. The roots, stems, leaves and leaf sheath were collected, and when the Xiushui 134 was in heading age, the young panicles were collected. All samples were frozen in liquid nitrogen and ground rapidly. Then the total RNA was extracted and reverse transcribed to obtain the cDNA. The expression of OsPEP1 in various tissues was detected by qRT-PCR. The results showed that the gene OsPEP1 was expressed in the different tissues tested in the present disclosure, and the expression level was higher in roots (A in FIG. 3). The detection primer sequences were as follows:

```
                                        (SEQ ID NO: 9)
        5'-GGCGTGGATGACGGGAGACT-3';

(SEQ ID NO: 10)
        5'-TACATCCTCATTCCTCGTTG-3',
```

The reaction system and procedures were as follows
2×Master: 2.5 µl
cDNA template: 0.1 µl
Primer-F (10 µM): 0.1 µl
Primer-R (10 µM): 0.1 µl
H₂O: 2.2 µl
Total: 5 µl;
The PCR procedures were as follows:
initiation: 95° C. for 1 minute;
amplification: 45 cycles of 95° C. for 10 seconds, 58° C. for 10 seconds, and 72° C. for 20 seconds;
Dissolution curve: 95° C. for 5 seconds, 65° C. for 1 minute, 97° C. cooling until 65° C.;
Cooling: 40° C. for 30 seconds;

2. The Expression of OsPEP1 in Different Rice Tissues Determined by GUS Staining.

The DNA of Xiushui 134 rice was extracted, and used as a template for PCR amplification to amplify the 2 kb nucleotide sequence of the OsPEP1 promoter. The primers for PCR amplification were as follows:

```
                                       (SEQ ID NO: 11)
   5'-GCATGCCTGCAGGTCGACGTTTCTCAGCTACGCCCCTG-3';

(SEQ ID NO: 12)
   5'-CCATGGTACCGTGGATCCCCGGAGCGCAGCCGTCGTCT-3',
```

The obtained PCR product was inserted between the SalI and BamHI restriction sites of the vector pBI101.3-GUSplus modified in our laboratory by recombinant cloning (Lv et al., 2014) to obtain the Pro$_{OsPEP1}$::GUS vector. The vector was verified to be correct by sequencing. The constructed overexpression vector was transferred into Agrobacterium EHA105 to transform Xiushui 134 plants, with reference to conventional steps, which were as follows:

(1) 500 µl of the cultured bacterial solution was added into a 1.5 ml centrifuge tube, centrifuged at room temperature, 4000 rmp for 2 minutes, and a resulting supernatant was removed. A suspension with 30 ml of AAM-infected bacterial solution containing 200 µmol/L acetosyringone was prepared, and the final concentration of bacterial solution indicated by OD$_{600}$ is 0.01; 80 to 120 rice calli grown to a certain size (about 1 cubic centimeter) were collected, put in Agrobacterium suspension, and shaken for 5 minutes on a horizontal shaker;

(2) the calli were taken out and placed on sterile filter paper to drain for 30 to 40 minutes;

(3) the calli were placed on a co-culture medium with a sterile filter paper, and cultured in the dark at 25° C. for 3 days;

(4) the calli were taken out, and then washed with sterile water for 5 to 6 times with constant shaking. The calli were washed twice with sterile water containing 300 mg/L carbenicillin sodium (Carb) and shaken on a horizontal shaker for 30 minutes each time. Finally, the calli were placed on sterile filter paper and drain for 2 hours;

(5) the air-dried calli were transferred to the selection medium containing 300 mg/L carbenicillin sodium with the corresponding selection pressure for a first round of selection, and cultured at 28° C. for 14 days in the light;

(6) the initial calli of the positive calli were transferred to the medium containing 300 mg/L carbenicillin sodium with the corresponding selection pressure for a second round of selection, and cultivated at 28° C. in the light until the granular calli with resistance emerged (about 14 days);

(7) 3 to 5 positive calli with bright yellow color were taken from different calli and then transferred into plastic jars with differentiation medium, sealed with parafilm, and put in a culture room (photoperiod: 16 hours of light) at constant temperature (25° C.) for differentiation into seedlings (about 40 days); and (8) when the seedlings grew to about 3 cm, the old roots and calli were cut off from the base of the seedlings with scissors, and put into the rooting medium to strengthen the seedlings (about 1 week). The seedlings with well-differentiated roots, stems and leaves were taken from the test tube (if the seedlings grew to the top of the test tube, open the lid in time), the sealing film was removed, an appropriate amount of distilled water or sterile water (to prevent the growth of bacteria in the medium) was added, and the seedlings were trained for 2 to 3 days. The agar was washed off and transplanted to grow in hydroponic conditions in the greenhouse. Primers for the gibberellin-resistant gene were used to detect transgenic plant, and sequences of the primer were as follows:

```
                                        (SEQ ID NO: 13)
5'-ATGAAAAAGCCTGAACTCACC-3';

(SEQ ID NO: 14)
5'-CTATTCCTTTGCCCTCGGACG-3',
```

In the obtained transgenic rice of T2 generation, representative lines (transgenic plants with positive GUS staining) were selected for GUS staining to study the expression of OsPEP1 in different tissues of rice. It was showed that the gene OsPEP1 was mainly expressed in rice roots, especially the root cap zone of the root tip, and the cortex of the meristem and mature zones (B-E in FIG. 3).

Example 3. Functional Study of the Gene OsPEP1 Encoding the Rice Peptide PEP1

1. Construction of the OsPEP1 Overexpressing Recombinant Vector

The mRNA of Xiushui 134 was extracted and reverse transcribed into cDNA, and the cDNA was used as a template for PCR amplification to prepare the OsPEP1 sequence (DNA set forth in SEQ ID NO: 3). Primers for PCR amplification were as follows:

```
                                        (SEQ ID NO: 15)
5'-ACGGGGACGAGCTCATGGGAGAGAAGGAGCGGAG-3';

(SEQ ID NO: 16)
5'-GACTCTAGAGGATCCCAACTGATGTTTACATCCTCA-3',
```

The obtained PCR product was inserted between the SacI and PstI restriction sites of the vector pCAMBIA1300 modified in our laboratory (Lv et al., 2014) by recombinant cloning to obtain the OsPEP1 overexpressing vector, and then the vector was verified to be correct by sequencing.

2. Acquisition of the OsPEP1 Overexpressing Transgenic Rice Plants

The OsPEP1 overexpressing vector constructed in step 1 was transferred into *Agrobacterium* EHA105 for transformation of rice Xiushui 134, and 32 positive transgenic plants were obtained. The specific steps were identical to step 2 of Example 2.

In the obtained T2 OsPEP1 overexpressing transgenic rice plants, three representative plants (OE1, OE2, OE3) were chosen for phenotypic analysis. It was showed that the primary root length of these transgenic plants were significantly shortened compared with that of Xiushui 134 (A and B in FIG. 4). The relative expression levels of endogenous OsPEP1 in Xiushui 134 and OsPEP1 overexpressing transgenic plants (OE1, OE2, OE3) were analyzed by quantitative real-time PCR (primers: GGCGTGGATGACGGGAGACT (SEQ ID NO: 9); TACATCCTCATTCCTCGTTG (SEQ ID NO: 10)). The results showed that the primary root length of those OsPEP1 overexpressing transgenic plants was positively correlated with the expression of OsPEP1 (see C in FIG. 4). In addition, the results of the observation of the section of these OsPEP1 overexpressing transgenic plants' root tips showed that the length of the meristematic region and the cell in the elongation region were significantly shortened, compared to that of Xiushui 134. Exogenous application of PEP1 could not restore the root tip defected phenotype of OsPEP1 overexpressing transgenic plants to the Xiushui 134 level (D-F in FIG. 4).

3. Construction of Recombinant OsPEP1 RNAi Vector

The mRNA of rice Xiushui 134 was extracted and reverse transcribed into cDNA, and the long cDNA was used as a template for PCR amplification to prepare a partial DNA sequence of OsPEP1:

```
                                        (SEQ ID NO: 17)
ACTCGGGAGAGAGGGAGCGCAGATTGTGCGTGAGGAAACGGATGGGAAGCA

GCGATTTCGATCGAGGGGCGCGATTTGGGGGCGTGGATGACGGGAGACTGG

GAGAGGGGACGAAGCGGTGTGAGGAGATGGTGGGAGCGATTTGGG.
```

Primers for PCR amplification were as follows:

```
                                        (SEQ ID NO: 18)
5'-ACTCGGGAGAGAGGGAGCGC-3';

(SEQ ID NO: 19)
5'-CCCAAATCGCTCCCACCATC-3',
```

The cloned PCR product was ligated with T vector (purchased from TAKARA), and the ligated plasmid was digested with PstI, BamH I and Pst I, Sal I respectively to obtain two fragments; the two fragments were ligated into the pBSSK-in vector (Wang et al. 2019) in two steps. pBSSK-in was first digested with Pst I and BamH I, and then ligated with one fragment, then digested with Nsi I and Sal I, and ligated with another fragment. Finally, the two fragments and intron were excised with Sac I and Sal I, and ligated into the same digested plant binary vector pCAMBIA1300 (Lv et al., 2014) to obtain an RNAi expression vector targeting OsPEP1. The RNAi expression vector targeting OsPEP1 was verified to be correct by sequencing.

4. Acquisition of OsPEP1 RNAi Transgenic Plants

The RNAi vector targeting OsPEP1 constructed in the above step 3 was transferred into *Agrobacterium* EHA105 for transformation of Xiushui 134, and 53 positive transgenic plants were obtained. The specific steps were identical to the step 2 in Example 2.

In the obtained T2 OsPEP1 RNAi transgenic plants, three representative plants (Ri1, Ri2, Ri3) were selected for phenotypic analysis. It was showed that the root length of these transgenic plants was significantly shortened compared to the wild type Xiushui 134 (see A and B in FIG. 5). The relative expression levels of endogenous OsPEP1 in Xiushui 134 and those OsPEP1 RNAi transgenic plants (Ri1, Ri2, Ri3) were analyzed by quantitative real-time PCR (primers: GGCGTGGATGACGGGAGACT (SEQ ID NO: 9); TACATCCTCATTCCTCGTTG (SEQ ID NO: 10)). The results showed that the length of the primary root of those transgenic plants was positively correlated with the expression of OsPEP1 (C in FIG. 5); and results of section showed that the length of the meristem and the cells in the elongation zone of the those transgenic plants were significantly shortened compared to that of Xiushui 134. Additionally, exogenous application of PEP1 could restore the root tip defected phenotype of OsPEP1 RNAi transgenic plants to the Xiushui 134 level (D-F in FIG. 5).

Collectively, through comparative study of 234 rice root secreted peptides identified by LC-MS/MS and 416 candidate genes encoding rice peptides, in combination with the genetic analysis, a root-secreted peptide PEP1 (Ser-Asp-Phe-Asp-Arg, SEQ ID NO: 1) associated with rice primary root development was identified and its encoding gene OsPEP1 (LOC_Os11g09560) was determined. The results of physiological experiments of the present disclosure showed that exogenous application of PEP1 inhibited rice root elongation, and the genetic analysis of the present disclosure showed that overexpression or inhibition of OsPEP1 expression inhibited rice root elongation. These results suggest that the rice root secreted peptide may play an important role in rice root development as a signaling molecule, and may control the growth and development of rice roots by regulating the expression of OsPEP1.

Finally, it should also be noted that the above enumeration is only a few specific embodiments of the present disclosure. Obviously, the present disclosure is not limited to the above embodiments, and many modifications can be made. All modifications by those skilled in the art that can be directly derived or associated from the present disclosure shall be considered to fall within the protection scope of the present disclosure.

What is claimed is:

1. A method for regulating root length of rice, the method comprising:
   overexpressing or inhibiting expression of a gene encoding the peptide of SEQ ID NO: 1,
   wherein overexpression of the gene encoding the peptide of SEQ ID NO: 1 comprises:
   inserting the nucleotide sequence set of SEQ ID NO: 3 into a multiple cloning site of plasmid pCAMBIA1300 to obtain a recombinant expression vector I-OsPEP1 overexpression vector; and
   introducing the recombinant expression vector I-OsPEP1 overexpression vector into the rice, and
   wherein the inhibition of the gene encoding the peptide of SEQ ID NO: 1 comprises:
   inserting the nucleotide sequence of SEQ ID NO: 3 ligated to a transition vector pBSSK-in in sense and antisense orientations, and then conducting insertion into a plasmid pCAMBIA1300 to obtain a recombinant expression vector II-OsPEP1 RNAi vector; and
   introducing the recombinant expression vector I-OsPEP1 RNAi vector into the rice.

* * * * *